United States Patent
Beeckler et al.

(10) Patent No.: US 12,311,132 B2
(45) Date of Patent: May 27, 2025

(54) VERIFYING PROPER WITHDRAWAL OF CATHETER INTO SHEATH

(71) Applicant: Biosense Webster (Israel) Ltd., Yokneam (IL)

(72) Inventors: Christopher Thomas Beeckler, Brea, CA (US); Ella Ozeri, Binyamina (IL); Aviva Goldberg, Yokneam (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 232 days.

(21) Appl. No.: 18/064,852

(22) Filed: Dec. 12, 2022

(65) Prior Publication Data

US 2023/0105708 A1    Apr. 6, 2023

Related U.S. Application Data

(63) Continuation of application No. 16/657,463, filed on Oct. 18, 2019, now Pat. No. 11,541,212.

(51) Int. Cl.
*A61M 25/10* (2013.01)
*A61B 17/221* (2006.01)
(Continued)

(52) U.S. Cl.
CPC ..... *A61M 25/10187* (2013.11); *A61B 17/221* (2013.01); *A61M 25/0074* (2013.01);
(Continued)

(58) Field of Classification Search
CPC ........ A61M 25/10187; A61M 25/0074; A61M 25/10181; A61M 2025/0166; A61M 2205/18; A61B 17/221; A61B 2017/00336; A61B 2017/00358; A61F 2/95; A61F 2/9517; A61F 2002/9528; A61F 2002/9534; A61F 2/958; A61F 2002/9583;
(Continued)

(56) References Cited

U.S. PATENT DOCUMENTS

| | | |
|---|---|---|
| 5,391,199 A | 2/1995 | Ben-Haim |
| 5,558,091 A | 9/1996 | Acker et al. |

(Continued)

FOREIGN PATENT DOCUMENTS

| | | |
|---|---|---|
| EP | 3053517 A1 | 8/2016 |
| EP | 3284404 A1 | 2/2018 |

(Continued)

OTHER PUBLICATIONS

Extended European Search Report issued in European Patent Application No. 20202308.1 dated Dec. 22, 2020.
(Continued)

*Primary Examiner* — Thomas McEvoy

(57) ABSTRACT

A method includes, in a processor, receiving signals from (i) a first position sensor disposed on a shaft of a catheter, and (ii) a second position sensor disposed on a distal end of a sheath of the catheter. Based on the signals received from the first position sensor and the second position sensor, an event is detected in which an expandable distal-end assembly of the catheter is being withdrawn into the sheath while still at least partially expanded. A responsive action is initiated in response to detecting the event.

17 Claims, 2 Drawing Sheets

(51) Int. Cl.
*A61M 25/00* (2006.01)
*A61B 17/00* (2006.01)
*A61B 18/00* (2006.01)
*A61M 25/01* (2006.01)

(52) U.S. Cl.
CPC .............. *A61M 25/10181* (2013.11); *A61B 2017/00336* (2013.01); *A61B 2017/00358* (2013.01); *A61B 2018/00577* (2013.01); *A61M 2025/0166* (2013.01); *A61M 25/10188* (2013.11); *A61M 2205/18* (2013.01)

(58) Field of Classification Search
CPC .............. A61F 2002/9586; A61F 2/962; A61F 2002/9623; A61F 2/966; A61F 2/9661; A61F 2/9662; A61F 2002/9665; A61F 2002/9505
See application file for complete search history.

(56) References Cited

U.S. PATENT DOCUMENTS

| | | | |
|---|---|---|---|
| 6,172,499 | B1 | 1/2001 | Ashe |
| 6,177,792 | B1 | 1/2001 | Fenster et al. |
| 6,690,963 | B2 | 2/2004 | Ben-Haim et al. |
| 6,748,255 | B2 | 6/2004 | Fuimaono et al. |
| 6,788,967 | B2 | 9/2004 | Ben-Haim et al. |
| 6,973,339 | B2 | 12/2005 | Govari |
| 7,371,232 | B2 | 5/2008 | Scheib |
| 7,756,576 | B2 | 7/2010 | Levin |
| 7,848,787 | B2 | 12/2010 | Osadchy |
| 7,869,865 | B2 | 1/2011 | Altmann et al. |
| 8,456,182 | B2 | 6/2013 | Bar-Tai et al. |
| 8,475,450 | B2 | 7/2013 | Beeckler et al. |
| 8,600,472 | B2 | 12/2013 | Beeckler et al. |
| 8,608,735 | B2 | 12/2013 | Altmann et al. |
| 9,050,010 | B2 | 6/2015 | Bouy et al. |
| 9,220,433 | B2 | 12/2015 | Ditter et al. |
| 9,788,893 | B2 | 10/2017 | Ditter et al. |
| 9,848,948 | B2 | 12/2017 | Foemono et al. |
| 2009/0262979 | A1* | 10/2009 | Markowitz ............ A61B 5/061 382/128 |
| 2013/0123694 | A1 | 5/2013 | Subramaniyan et al. |
| 2013/0303886 | A1 | 11/2013 | Bar-Tal et al. |
| 2014/0275991 | A1 | 9/2014 | Potter et al. |
| 2016/0120598 | A1 | 5/2016 | Brink et al. |
| 2017/0100188 | A1 | 4/2017 | Clark et al. |

FOREIGN PATENT DOCUMENTS

| | | |
|---|---|---|
| JP | 2013233438 A | 11/2013 |
| JP | 2016144642 A | 8/2016 |
| JP | 2017109101 A | 6/2017 |
| WO | 96/05768 A1 | 2/1996 |

OTHER PUBLICATIONS

Exam Report dated Dec. 8, 2023, from corresponding European Application No. 20202308.1.
Search Report dated Mar. 27, 2024, from corresponding Japanese Application No. 2020-174505.
Notification of Reasons for Refusal dated Apr. 16, 2024, from corresponding Japanese Application No. 2020-174505.
Decision to Grant a Patent dated Jul. 16, 2024, from corresponding Japanese Application No. 2020-174505.

* cited by examiner

VERIFYING PROPER WITHDRAWAL OF CATHETER INTO SHEATH

CROSS-REFERENCE TO RELATED APPLICATIONS

This application is a continuation application of U.S. patent application Ser. No. 16/657,463 filed 18 Oct. 2019, the entire contents of which is incorporated herein by reference as if fully set forth below.

FIELD OF THE INVENTION

The present invention relates generally to tracking a probe position and/or shape within a living body, and specifically to tracking balloon catheters.

BACKGROUND OF THE INVENTION

Techniques for tracking a position and/or shape of intra-body probes, such as catheters, were previously proposed in the patent literature. For example, U.S. Patent Application Publication 2013/0303886 describes an apparatus, including a sheath configured to be inserted into a human patient, the sheath including a lumen and a sheath distal end. The apparatus further includes a probe, having a probe distal end which is configured to be inserted through the lumen into the human patient. A magnetic transducer is fixedly attached to the sheath distal end and is transmitting a magnetic field which a sensor disposed on the distal end of a probe is picking up, allowing for a relative distance measurement between the distal ends of the probe and the sheath.

As another example, U.S. Pat. No. 6,748,255 describes a basket catheter comprising a basket assembly that has proximal and distal ends, and electrodes mounted on a plurality of spines connected at their proximal and distal ends. The catheter further comprises a distal location sensor mounted at or near the distal end of the basket-assembly and a proximal location sensor mounted at or near the proximal end of the basket assembly. In use, the coordinates of the distal location sensor relative to those of the proximal sensor can be determined and taken together with known information pertaining to the curvature of the spines of the basket assembly to find the positions of at least one electrode in each spine.

SUMMARY OF THE INVENTION

An embodiment of the present invention provides a method including, in a processor, receiving signals from (i) a first position sensor disposed on a shaft of a catheter, and (ii) a second position sensor disposed on a distal end of a sheath of the catheter. Based on the signals received from the first position sensor and the second position sensor, an event is detected in which an expandable distal-end assembly of the catheter is being withdrawn into the sheath while still at least partially expanded. A responsive action is initiated in response to detecting the event.

In some embodiments, detecting the event includes estimating an extent to which the distal-end assembly is expanded, and detecting the event based on the signals received from the first position sensor and the second position sensor, and on the estimated extent to which the distal-end assembly is expanded.

In some embodiments, the first position sensor is fitted on a proximal side of the distal-end assembly.

In an embodiment, receiving the signals further includes receiving signals from a third position sensor fitted on a distal side of the distal-end assembly, and wherein detecting the event is performed based on the signals received from the first position sensor, the second position sensor and the third position sensor.

In another embodiment, detecting the event includes (a) estimating relative positions of the first position sensor, the second position sensor and the third position sensor based on the signals, (b) based on the relative positions of the first position sensor, the second position sensor and the third position sensor, estimating (i) sufficiency of collapse of the expandable distal-end assembly, and (ii) sufficiency of distal distance of the expandable distal-end assembly from the distal edge of the sheath, and (c) detecting the event responsively to the sufficiency of collapse and sufficiency of distal distance.

In some embodiments, calculating the positions includes calculating projections of the positions on a longitudinal axis defined by the distal end of the shaft.

In some embodiments, estimating the sufficiency of collapse includes calculating a length between the estimated position of the first position sensor and the estimated position of the third position sensor, and comparing the calculated distance to a prespecified minimal length.

In an embodiment, estimating the sufficiency of distal distance includes calculating a distance between the estimated position of the first position sensor and the estimated position of the second position sensor, and comparing the calculated distance to a prespecified minimal distance.

In another embodiment, initiating the responsive action includes issuing a warning to a physician.

In some embodiments, the expandable distal-end assembly includes an inflatable balloon.

In some embodiments, initiating the responsive action includes reducing a rate of pumping fluid into the balloon to an idle flow rate.

In an embodiment, the expandable distal-end assembly includes one of an expandable basket or lasso type end effector.

There is additionally provided, in accordance with an embodiment of the present invention, a medical device including a sheath, a shaft, a first location sensor and a second location sensor. The sheath extends a long a longitudinal axis. The shaft is disposed in the sheath and configured to extend out of the sheath along the longitudinal axis, with the shaft including an expandable member connected to a distal portion of the shaft. The first location sensor is coupled to the shaft to provide signals representative of a location of the shaft. The second location sensor is coupled to a distal portion of the sheath to provide signals representative of a location of the sheath so that a location or direction of movement of the shaft with respect to the sheath can be obtained with the first and second location sensors.

There is further provided, in accordance with an embodiment of the present invention, a system including a catheter, a sheath, and a processor. The catheter includes a shaft, and a first position sensor coupled to the shaft. The sheath has a second position sensor disposed on a distal end thereof. The processor is configured to: (a) based on the signals received from the first position sensor and the second position sensor, detect an event in which an expandable distal-end assembly of the catheter is being withdrawn into the sheath while still at least partially expanded, and (b) initiate a responsive action in response to detecting the event.

The present invention will be more fully understood from the following detailed description of the embodiments thereof, taken together with the drawings in which:

DETAILED DESCRIPTION OF EMBODIMENTS

Overview

Figure 1:
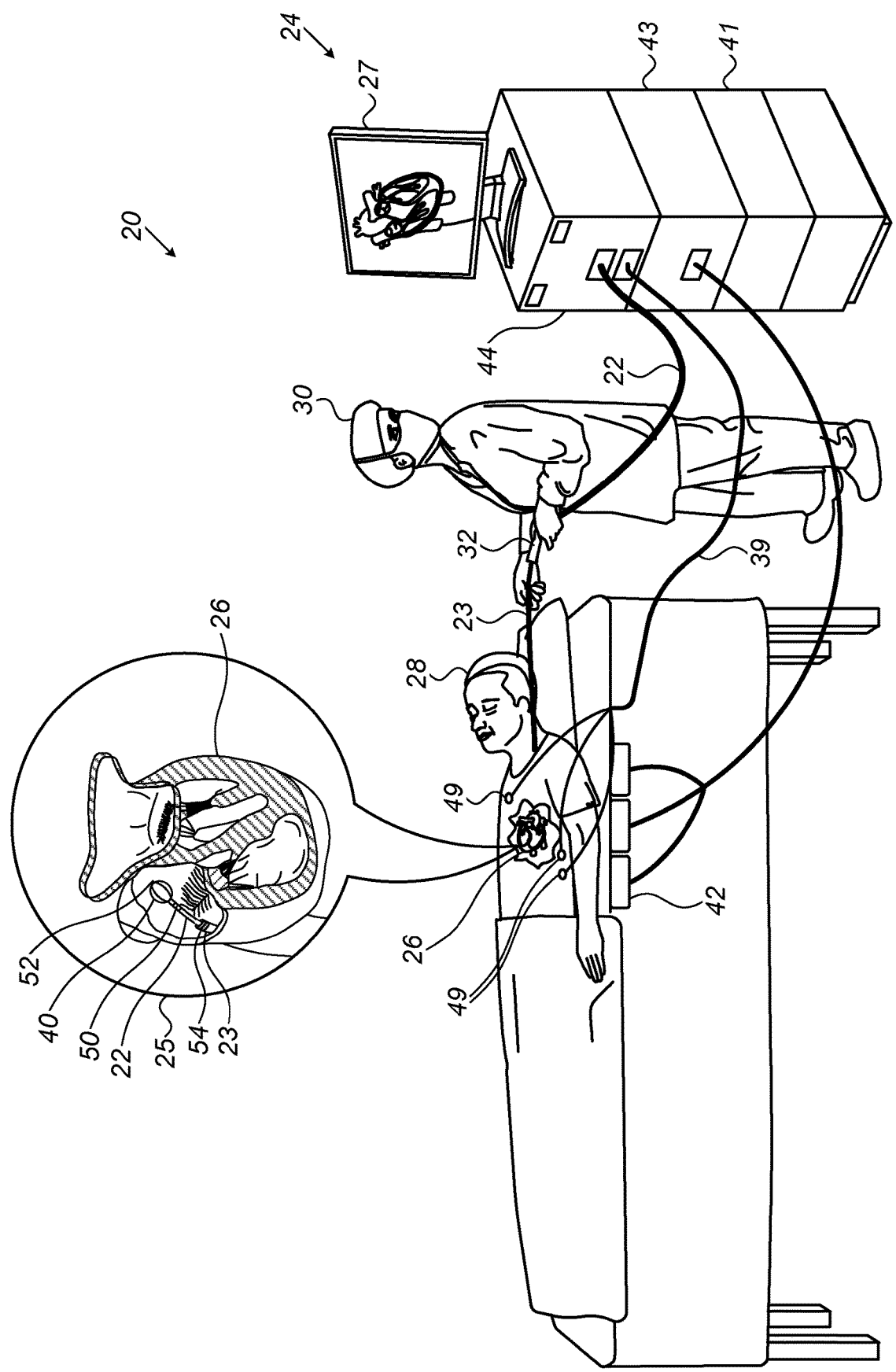
FIG. 1 is a schematic pictorial illustration of a catheter position tracking system that tracks a balloon catheter inside the heart of a patient, in accordance with an embodiment of the present invention.

An expandable distal-end assembly of a catheter for insertion into a cavity of an organ of a patient, such as a balloon catheter or a basket catheter, may be employed in various clinical applications, such as electro-anatomical mapping and ablation of the cavity walls, e.g., cardiac chamber walls. The expandable distal-end assembly is coupled to the distal end of a shaft.

In a typical procedure, the catheter is inserted into the heart through a sheath with the distal-end assembly in a collapsed configuration. After exiting the sheath inside the heart, the distal-end assembly is expanded to an expanded configuration. Withdrawal (retraction) of the catheter back into the sheath is accomplished manually, by collapsing the distal-end assembly as described below. During the withdrawal process, it is difficult for a physician to know the exact status of the catheter, for example whether the distal-end assembly is sufficiently collapsed, and to what extent the catheter is retracted into the distal end of the sheath.

Consider, for example, a balloon catheter. While in position outside the sheath, the balloon catheter is expanded or collapsed using a balloon advancement member. Withdrawal of a collapsed balloon from the body is done by pushing the advancement member distally to elongate and deflate the balloon. The shaft of the catheter is then pulled back to retract the deflated balloon into the sheath. However, if the physician has not verified that the balloon is properly elongated (i.e., fully collapsed) during the withdrawal phase, the withdrawal will require excessive force and may damage the catheter.

Embodiments of the present invention that are described hereinafter combine knowledge of sufficiency of balloon collapse, and sufficiency of balloon distal distance from the distal end of the sheath, so as to verify proper withdrawal of the balloon from the body of a patient. In some embodiments, a processor determines, during a balloon withdrawal session, that (i) the balloon is insufficiently collapsed and (ii) the balloon is already at least partially inside the sheath. In such a case, a warning is issued to the physician that withdrawal is being attempted while the balloon is not ready for withdrawal (i.e., the balloon is still too expanded). Furthermore, the processor may initiate steps to amend the situation, as described below.

In some embodiments, a processor receives signals from (i) a first position sensor disposed on a shaft of a catheter, and (ii) a second position sensor disposed on a distal end of a sheath of the catheter. Based on the signals received from the first position sensor and the second position sensor, the processor detects an event in which an expandable distal-end assembly of the catheter is being withdrawn into the sheath while still at least partially expanded, and initiates a responsive action in response to detecting the event. In an embodiment, detecting the event includes estimating an extent to which the distal-end assembly is expanded, and detecting the event based on the signals received from the first position sensor and the second position sensor, and on the estimated extent to which the distal-end assembly is expanded.

In another embodiment, the processor is further configured to receive the signals by receiving signals from a third position sensor fitted on a distal side of the distal-end assembly, and wherein detecting the event is performed based on the signals received from the first position sensor, the second position sensor and the third position sensor.

In other embodiments, the processor receives signals from (i) a first, proximal position sensor and a third, distal position sensor disposed on a shaft of a catheter, on either side of an expandable distal-end assembly (e.g., a balloon) fitted at a distal end of the shaft, and (ii) a second, sheath position sensor disposed on a distal end of a sheath of the catheter. Based on the signals received from the proximal position sensor, the distal position sensor and the sheath position sensor, the processor detects an event in which the expandable distal-end assembly is being withdrawn into the sheath while still at least partially expanded, and initiates a responsive action in response to detecting the event, such as warning a physician.

In some embodiments, the processor determines that the balloon is insufficiently collapsed by comparing the length of the balloon, E, to a prespecified minimum collapsed length $E_0$. The processor determines that the balloon has an insufficient distal distance from the distal edge of the sheath (e.g., that the balloon is at least partially inside the sheath) by comparing a measured distance, $\Delta$, between the proximal position sensor on the shaft and a location over the distal end of the sheath to a minimum length $\Delta_0$. In an embodiment, if $E \leq E_0$ and $\Delta \leq \Delta_0$, the processor determines that withdrawal is being attempted while the balloon is not sufficiently collapsed, and issues a warning.

Additionally or alternatively to the warning, the processor may reduce the rate of pumping fluid into the balloon (which, if too high, causes the balloon to remain inflated) to an idle flow rate. Further additionally or alternatively, any other suitable responsive action can be taken.

Distance $\Delta$ is measured using one or more additional position sensors, which are disposed on the distal end of the sheath, and termed hereinafter "sheath position sensor." Based on position signals from the sheath position sensor, the processor of the system can calculate the distance between the positions of the proximal balloon sensor and the sheath sensor along a longitudinal axis defined by the distal end of the shaft. Using the calculated distance, and known catheter geometry, the processor can compare distance $\Delta$ to the prespecified minimum distance, $\Delta_0$.

The sheath position sensor is typically a magnetic position sensor. But other sensor types could be used to enable a processor to derive the relative positions of the sheath distal end and the balloon proximal sensor, based on positions measured in in the coordinate system used by the processor. For example, the sheath sensor could be an electrode disposed on the distal end of the sheath.

Typically, the processor is programmed in software containing a particular algorithm that enables the processor to conduct each of the processor related steps and functions outlined above.

By combining sufficiency of balloon distal position relative to the sheath and a sufficiency of balloon collapse, embodiments of the present invention enable a physician operating the balloon catheter to safely retract the balloon into a sheath.

The embodiments described herein refer mainly to balloon catheters, by way of example. The disclosed technique, however, is equally applicable to other kinds of expandable/collapsible distal-end assemblies, such as basket catheters.

System Description

FIG. 1 is a schematic pictorial illustration of a catheter position tracking system 20 that tracks a balloon catheter inside the heart of a patient, in accordance with an embodiment of the present invention. The shown system 20 includes both electric and magnetic position tracking sub-systems. System 20 is used to determine the position of a balloon catheter 40, seen in an inset 25, fitted at a distal end of a shaft 22, and an extent to which the balloon is collapsed before a balloon withdrawal attempt through a sheath 23. Typically, balloon catheter 40 is used for therapeutic treatment, such as spatially ablating cardiac tissue, for example at the left atrium.

Balloon catheter 40 incorporates a proximal position sensor 50 and a distal position sensor 52 fitted on shaft 22, on either side of the balloon. A sheath position sensor 54 is disposed on a distal end of sheath 23 of the catheter. Proximal position sensor 50 and distal position sensor 52 are connected by wires running through shaft 22 to various driver circuitries in a console 24. Sheath position sensor 54 is disposed at a distal portion of the sheath 23 (FIG. 2) and connected by wires running initially through sheath 23, and are subsequently connected to the various driver circuitries in a console 24.

Typically, proximal position sensor 50, distal position sensor 52, and sheath position sensor 54, comprise either a magnetic sensor or an electrode. The magnetic sensor, or the electrode, is used by the magnetic or electric position tracking sub-systems, respectively, as described below.

Physician 30 navigates balloon catheter 40 to a target location in a heart 26 of a patient 28 by manipulating shaft 22 using a manipulator 32 near the proximal end of the catheter and/or deflection from sheath 23. Balloon catheter 40 is inserted, in a collapsed configuration, through sheath 23, and only after sheath 23 is retracted and balloon advancement member is subsequently retracted does balloon catheter 40 regain its intended functional shape. By containing balloon catheter 40 in a folded configuration, sheath 23 also serves to minimize vascular trauma on its way to the target location.

Console 24 comprises a processor 41, typically a general-purpose computer, with suitable front end and interface circuits 44 for receiving signals from various sensors inside and on patient 28.

In some embodiments, processor 41 accurately determines position coordinates of proximal position sensor 50, distal position sensor 52, and sheath position sensor 54 inside heart 26. Examples of processor coordinate systems may include those used by various position tracking systems, such as the aforementioned electric and magnetic position tracking sub-systems.

In an embodiment, processor 41 determines the position coordinates, which are based on, among other inputs, measured impedances between an electrode serving as one or more position sensors 50, 52, and 54, and surface electrodes 49. Processor 41 is connected to surface electrodes 49, which are seen in the exemplified system as attached to the skin of patient 28, by wires running through a cable 39 to the chest of patient 28.

The method of electrode position sensing using an electrical position tracking sub-system of system 20 is implemented in various medical applications, for example using the Advanced Catheter Location (ACL) method in the CARTO™ system, produced by Biosense-Webster Inc. (Irvine, California) and is described in detail in U.S. Pat. Nos. 7,756,576, 7,869,865, 7,848,787, and 8,456,182, which prior application is hereby incorporated by reference in its entirety herein into this application as if set forth in full with a copy in the Appendix of priority patent application U.S. Ser. No. 16/657,463.

Using sensed electrode position, a shape of a multielectrode catheter, such as a balloon catheter, a basket catheter, a LASSO™ or NMARQ™ catheters (both made by Biosense Webster) as well as other multi-electrode deflectable catheters, can be estimated, and a degree of collapse (or straitening) estimated, of a respective expendable, or deflectable, distal end assembly. Examples of a catheter having an end effector in the form of a lasso are shown and described in U.S. Pat. Nos. 9,788,893; 6,973,339; 8,475,450; 8,600,472; 9,050,010; 9,220,433; 9,848,948; 8,608,735; 7,371,232; US2017/0100188, which are all incorporated by reference as if set forth in full herein. Therefore, together with the known distance between a proximal sensor and a sheath sensor, the ACL method can be used with disclosed embodiments of the invention which do not include a distal position sensor to detect an event in which the expandable distal-end assembly is being withdrawn into the sheath while still at least partially expanded, or deflected.

For example, the aforementioned U.S. Pat. No. 8,456,182 with a 'local scaling' process called hereinafter 'Independent Current Location' (ICL) are applicable to catheters having a plurality of sensing-electrodes disposed over their distal end. Using a known spatial relationship among two or more electrodes, e.g., one or more known distances between electrodes, the ICL process is able to scale the relative positions of a plurality of electrodes so as to exactly estimate a shape of the expendable distal end assembly of the catheter.

In some embodiments, the disclosed method uses the sheath location sensor and the proximal location sensor with the ACL and ICL derived shape of the expandable distal end assembly to detect an event in which the expandable distal-end assembly is being withdrawn into the sheath while still at least partially expanded, or deflected. In such embodiments, the distal position sensor may be omitted.

In general, there can be numerous techniques to estimate the shape of the expandable distal end assembly (and specifically to estimate the extent to which the distal end assembly is expanded). As another example, the shape can be estimated using magnetic position sensors disposed over the expandable distal end assembly. For example, U.S. application Ser. No. 16/198,487, of Nov. 21, 2018, titled, "Configuring Perimeter of Balloon Electrode as Location Sensor," published as US 2020/0155224, describes multiple magnetic coils disposed over a balloon to serve as position sensors, which document is incorporated by reference with a copy provided in the Appendix of priority patent application U.S. Ser. No. 16/657,463.

In U.S. application Ser. No. 16/198,487, published as US 2020/0155224, a spatial configuration of the expandable balloon inside the organ is estimated. It is noted there that the estimating may include estimating at least one of a deflection of the balloon relative to a longitudinal axis defined by the distal end of the shaft and estimating a shape of the balloon inside the organ. The step of estimating a shape may include identifying an extent of expansion of the balloon or detecting whether the balloon is fully expanded or not.

In an embodiment, a balloon shape is estimated in a form of an "inflation index," that gives a level of balloon inflation in a dimensionless number. Similarly, an expansion index may be provided with any expandable distal end assembly.

As noted above, system 20 further comprises a magnetic-sensing sub-system. Patient 28 is placed in a magnetic field generated by a pad containing magnetic field generator coils 42, which are driven by unit 43. The magnetic fields generated by coils 42 generate signals in any magnetic position sensor, which are then provided as corresponding electrical inputs to processor 41, which uses these to calculate the position of any of position sensors 50, 52, and 54 that comprise a magnetic sensor.

The method of position sensing using external magnetic fields is implemented in various medical applications, for example, in the CARTO™ system, produced by Biosense Webster Inc., and is described in detail in U.S. Pat. Nos. 5,391,199; 5,558,091; 6,172,499; 6,177,792; 6,788,967 and 6,690,963, and in PCT Patent Publication WO 96/05768, whose disclosures are all incorporated herein by reference with a copy provided in the Appendix of priority patent application U.S. Ser. No. 16/657,463.

Using the tracked positions, console 24 may drive a display 27, which shows the distal end of the catheter position inside heart 26.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm that enables processor 41 to perform the disclosed steps, as described in FIG. 3.

FIG. 1 only exemplifies a few techniques related to the disclosed invention for the sake of simplicity and clarity. For example, another electrical-based position measurement method can be used, in which voltage gradients are applied between surface electrodes 49, and position signals are derived from the resulting voltage measurements of the intrabody electrodes.

Example techniques for estimating the degree of elongation of an expandable assembly are described in U.S. patent application Ser. No. 16/234,604, filed Dec. 28, 2018, entitled "Finding Elongation of Expandable Distal End of Catheter," published as US2020/0206461, which is assigned to the assignee of the present patent application and whose disclosure is incorporated herein by reference.

Verifying Withdrawal of Balloon Catheter into Sheath

Figure 2:
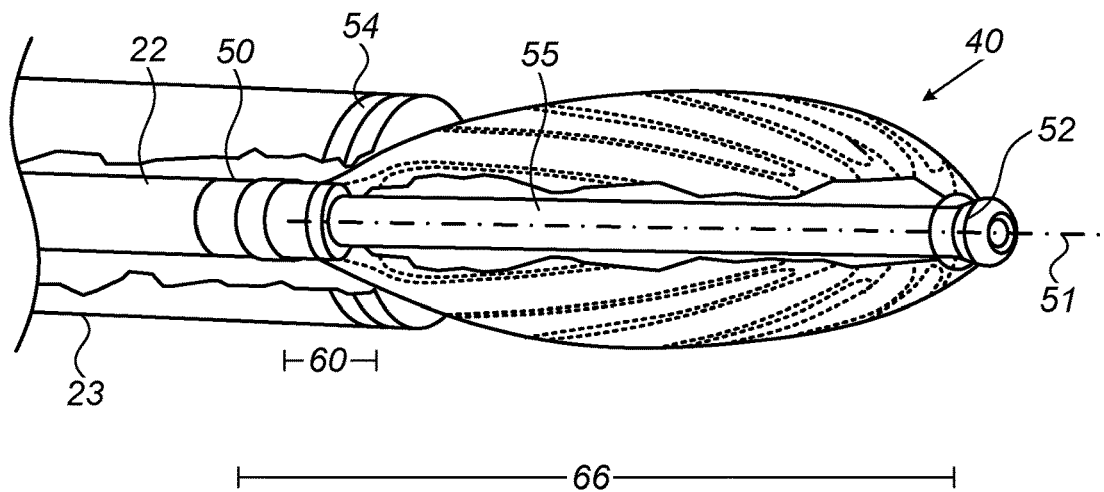
FIG. 2 is a schematic pictorial illustration of the balloon catheter of FIG. 1, in accordance with an embodiment of the present invention.

FIG. 2 is a schematic pictorial illustration of the balloon catheter of FIG. 1, in accordance with an embodiment of the present invention. Balloon 40 is fitted at a distal end of shaft 22, which defines a longitudinal axis 51. Proximal position sensor 50 is fitted on shaft 22, while distal position sensor 52 is fitted on distal end of balloon advancement member 55, so that position sensors reside on either side of balloon 40, which is seen in FIG. 2 in a partially collapsed configuration. Also seen is sheath position sensor 54 fitted on the distal end of sheath 23.

The balloon 40 catheter is at least partially collapsed and deflated after the physician has pushed an advancement member 55 distally to elongate and deflate balloon 40.

In the disclosed technique, processor 41 calculates a distance 60, $\Delta$, between the positions of sheath position sensor 54 and proximal position sensor 50 and along longitudinal axis 51. If proximal position sensor 50 is sufficiently inside sheath 23 to pass over sheath position sensor 54 then distance 60 is negative, i.e., $\Delta < 0$. Processor 41 further calculates a length 66, E, of balloon 40 by calculating the distance between the positions of proximal position sensor 50 and the distal position sensor 52 along longitudinal axis 51.

Based on comparing distance 60 and length 66 to a prespecified minimal distance, $\Delta_0$, and a prespecified minimal length, $E_0$, respectively, processor 41 can determine if a balloon withdrawal into sheath 23 is attempted while balloon 40 is insufficiently collapsed.

The illustration shown in FIG. 2 is chosen purely for the sake of conceptual clarity. Elements which are not relevant to the disclosed embodiments of the invention, such as additional sensors, are omitted for the sake of clarity. As noted above, in some embodiments, using the sheath location sensor and the proximal position sensor with the derived shape (e.g., using ACL and ICL, or other means) of the expandable distal end assembly (e.g., one comprising a balloon), an event is detected in which the expandable distal-end assembly is being withdrawn into the sheath while still at least partially expanded.

Figure 3:
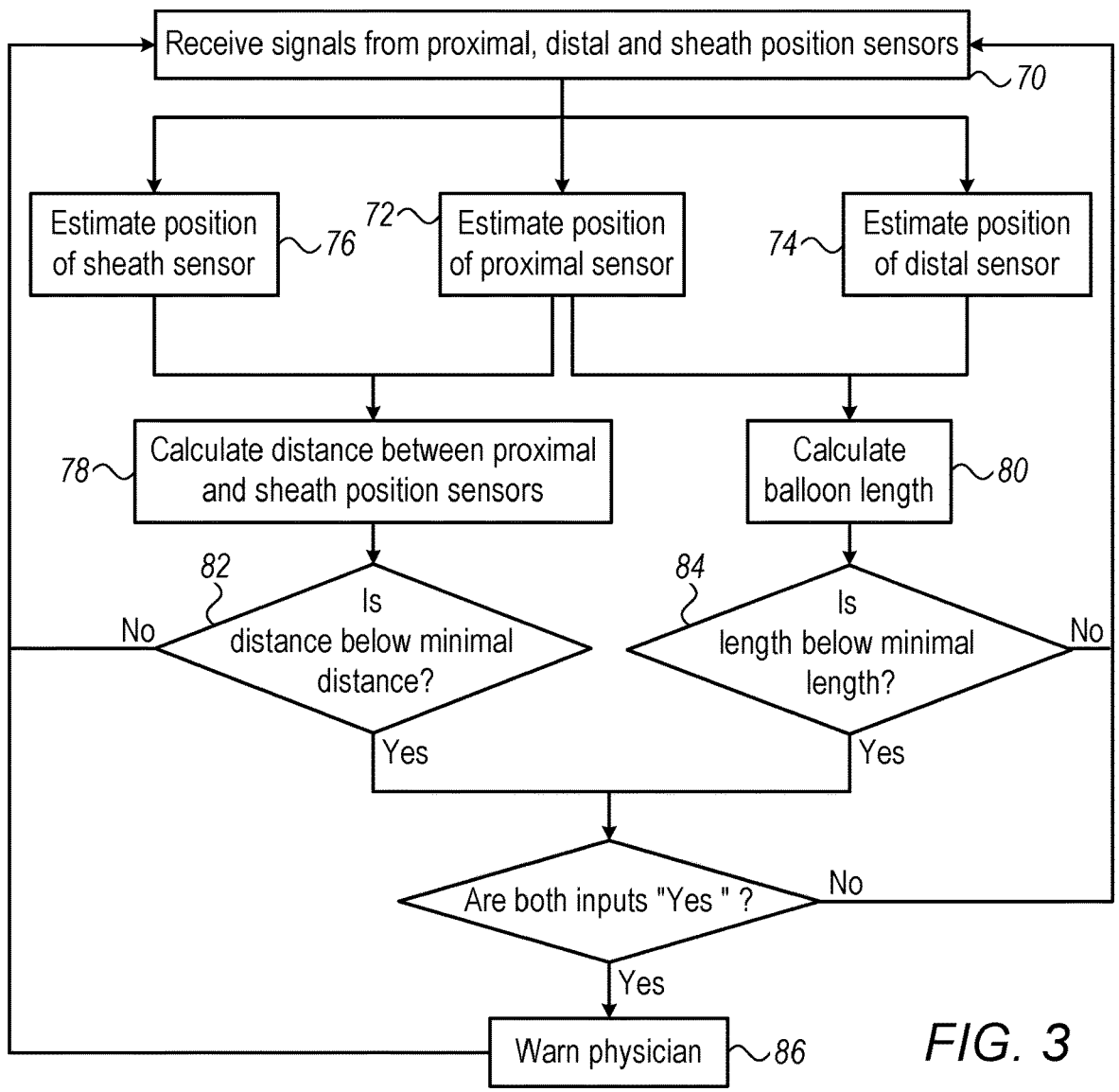
FIG. 3 is a flow chart that schematically illustrates a method for verifying withdrawal of the balloon catheter of FIG. 2 into a sheath, in accordance with an embodiment of the present invention.

FIG. 3 is a flow chart that schematically illustrates a method for verifying withdrawal of balloon 40 of FIG. 2 into sheath 23, in accordance with an embodiment of the present invention. The algorithm, according to the presented embodiment, carries out a process that begins with processor 41 receiving signals from proximal position sensor 50, distal position sensor 52, and sheath position sensor 54, at a position signals receiving step 70.

Next, using the position signals, processor 41 estimates positions of proximal position sensor 50, distal position sensor 52, and sheath position sensor 54, at position estimations steps 72, 74, and 76, respectively. In an embodiment, the processor is configured to calculate the positions by calculating projections of the positions on longitudinal axis 51.

At a distance 60 calculation step 78, processor 41 uses the positions calculated at steps 74 and 76 to calculate distance 60 of balloon 40 from the distal edge of sheath 23.

At a length 66 calculation step 80, processor 41 uses the positions calculated at steps 72 and 74 to calculate length 66, E, of balloon 40 from the distal edge of sheath 23.

Using distance 60, processor 41 estimates an insufficiency of distal distance of the inflatable balloon from the distal edge of the sheath, e.g., by checking if $\Delta \le \Delta_0$, as described above, at a sufficiency of distal distance estimation step 82.

Using length 66, processor 41 estimates an insufficiency of collapse of the inflatable balloon, e.g., by checking if $E \le E_0$, as described above, at a sufficiency of collapse estimation step 84.

If either of the answers to the questions in steps 82 and 84 is negative, processor 41 loops back the process to step 70 to continue monitoring the distal distance of balloon from sheath and if the balloon is sufficiently collapsed.

If both distal distance and collapse are deemed insufficient (i.e., both answers are "Yes"), processor 41 warns physician 30 that a withdrawal of the balloon into sheath is being attempted while the balloon is not sufficiently collapsed, at a warning step 86. In any event, the process goes back to step 70 to collect new position data.

The example flow chart shown in FIG. 3 is chosen purely for the sake of conceptual clarity. Additional steps may follow, such as reducing fluid pumping rate to assist in collapsing balloon 40.

Although the embodiments described herein mainly address balloon catheters, the methods and systems described herein can also be used with other types of catheters having an expandable distal end, such as with basket catheters, loop catheters that require the loop to be in the maximum expanded position, and deflectable catheters that require the catheter to be undeflected prior to withdrawing the catheter into the sheath. For loop and deflectable catheters, the diameter of the loop or the curvature of the catheter is the critical factor to monitor, while the distance E is secondary.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical device, the system comprising:
    a medical device comprising:
        a sheath that extends along a longitudinal axis;
        a shaft disposed in the sheath and configured to extend out of the sheath along the longitudinal axis, the shaft including an expandable member connected to a distal portion of the shaft;
        a first location sensor coupled to the shaft to provide signals representative of a location of the shaft;
        a second location sensor coupled to a distal portion of the sheath to provide signals representative of a location of the sheath so that a location or direction of movement of the shaft with respect to the sheath can be obtained with the first and second location sensors;
        surface electrodes; and
    a processor configured to:
        determine the location of the shaft in an organ of a patient based at least in part on the signals from the first location sensor received by the surface electrodes; and
        based on respective signals received from the first location sensor and the second location sensor, detect an event in which the expandable member is being withdrawn into the sheath while still at least partially expanded.

2. The system of claim 1, wherein the signals provided by the second location sensor are representative of a location of the sheath in an organ of a patient.

3. The system of claim 1, the first location sensor being disposed on a distal side of the expandable member.

4. The system of claim 1, the first location sensor being disposed on a proximal side of the expandable member.

5. The system of claim 4 further comprising a third location sensor disposed on a distal side of the expandable member.

6. The system of claim 5, wherein the processor is further configured to:
    based on respective signals received from the first location sensor, the second location sensor, and the third location sensor, detect the event in which the expandable member is being withdrawn into the sheath while still at least partially expanded.

7. The system of claim 6, wherein, based on relative positions of the first location sensor, the second location sensor, and the third location sensor, the processor is further configured to:
    estimate (i) sufficiency of collapse of the expandable member, and (ii) sufficiency of distal distance of the expandable member from the distal portion of the sheath; and
    detect the event responsively to the sufficiency of collapse and sufficiency of distal distance.

8. The system of claim 7, wherein the processor is configured to calculate the relative positions of the first location sensor, the second location sensor, and the third location sensor by calculating projections of the relative positions on a longitudinal axis defined by a distal end of the shaft.

9. The system of claim 7, wherein the processor is configured to estimate the sufficiency of collapse by calculating a length between the relative positions of the first location sensor and the third location sensor, and comparing the calculated length to a prespecified minimal length.

10. The system of claim 7, wherein the processor is configured to estimate sufficiency of distal distance by calculating a distance between the relative positions of the first location sensor and the second location sensor, and comparing the calculated distance to a prespecified minimal distance.

11. The system of claim 1, wherein the expandable member comprises an inflatable balloon.

12. The system of claim 1, wherein the expandable member comprises a basket assembly.

13. The system of claim 1, wherein the processor is further configured to initiate a responsive action in response to detecting the event.

14. The system of claim 13, wherein the processor is configured to detect the event by estimating an extent to which the expandable member is expanded based at least in part on the signals received from the first location sensor and the second location sensor.

15. The system of claim 1, wherein the processor is further configured to determine the location of the sheath in an organ of the patient based at least in part on the signals received by the surface electrodes from the second location sensor.

16. A system, comprising:
    a catheter comprising a shaft, a first position sensor, and an expandable member coupled to a distal portion of the shaft;
    a sheath configured to receive the shaft and comprising a second position sensor disposed on a distal end thereof; and a processor configured to:
  receive respective signals from the first position sensor and the second position sensor;
  based at least in part on the respective signals:
    calculate a distance between the first position sensor and the second position sensor;
    detect an event in which the expandable member is being withdrawn into the sheath while still at least partially expanded;
    estimate (i) sufficiency of collapse of the expandable member, and (ii) sufficiency of distal distance of the expandable member from the distal end of the sheath; and
    in response to determining the expandable member is insufficiently collapsed and the distal distance of the expandable member from the distal end of the sheath is less than a minimal distance, output a warning signal.

17. A system, comprising:
a catheter comprising:
  a shaft;
  an expandable member coupled to a distal end of the shaft;
  a first position sensor disposed proximal to the expandable member;
  a second position sensor disposed distal to the expandable member;
a sheath configured to receive the shaft and the expandable member and comprising a third position sensor; and
a processor configured to:
  receive respective signals from the first position sensor, the second position sensor, and the third position sensor;
  based at least in part on the respective signals:
    detect an event in which the expandable member is being withdrawn into the sheath while still at least partially expanded; and
    estimate (i) sufficiency of collapse of the expandable member, and (ii) sufficiency of distal distance of the expandable member from a distal portion of the sheath; and
    detect the event in response to the sufficiency of collapse and sufficiency of distal distance.

* * * * *